US011867645B2

(12) United States Patent
Grof et al.

(10) Patent No.: US 11,867,645 B2
(45) Date of Patent: Jan. 9, 2024

(54) SYSTEM AND METHOD FOR DETECTION AND IDENTIFICATION OF FOREIGN ELEMENTS IN A SUBSTANCE BY X-RAY OR GAMMA-RAY DETECTION AND EMISSION

(71) Applicant: Security Matters LTD., D.N. Hevel Eilot (IL)

(72) Inventors: Yair Grof, Rehovot (IL); Dmitrijs Docenko, Jerusalem (IL); Mor Kaplinsky, Herzliya (IL); Haggai Alon, Kibbutz Naan (IL); Yifat Bareket, Reut (IL); Michal Firstenberg, Rehovot (IL); Avital Trachtman, Lod (IL); Nachum Holin, Kibbutz Kfar-Aza (IL); Nadav Yoran, Tel Aviv (IL)

(73) Assignee: Security Matters LTD.

( * ) Notice: Subject to any disclaimer, the term of this patent is extended or adjusted under 35 U.S.C. 154(b) by 0 days.

(21) Appl. No.: 17/285,167

(22) PCT Filed: Oct. 18, 2019

(86) PCT No.: PCT/IB2019/001141
§ 371 (c)(1),
(2) Date: Apr. 14, 2021

(87) PCT Pub. No.: WO2020/079486
PCT Pub. Date: Apr. 23, 2020

(65) Prior Publication Data
US 2021/0325323 A1 Oct. 21, 2021

Related U.S. Application Data

(60) Provisional application No. 62/747,293, filed on Oct. 18, 2018.

(51) Int. Cl.
*G01N 23/2204* (2018.01)
*G01N 23/223* (2006.01)
(Continued)

(52) U.S. Cl.
CPC ........... *G01N 23/223* (2013.01); *G01N 23/22* (2013.01); *G01N 23/2204* (2013.01);
(Continued)

(58) Field of Classification Search
CPC ............... G01N 23/22; G01N 23/2204; G01N 23/2206; G01N 23/223; G01N 2223/076;
(Continued)

(56) References Cited

U.S. PATENT DOCUMENTS 4,212,397 A    7/1980  Bockelmann
6,130,931 A *  10/2000 Laurila ............... G01N 23/223
                                                    378/45
(Continued)

FOREIGN PATENT DOCUMENTS

EP      1870698 A1    12/2007
JP      H05249055 A    9/1993
(Continued)

OTHER PUBLICATIONS

Partial International Search Report including Provisional Opinion for Application No. PCT/IB2019/001141, dated Apr. 29, 2020, pp. 1-11.
(Continued)

*Primary Examiner* — Allen C. Ho
(74) *Attorney, Agent, or Firm* — Lerner David LLP

(57) ABSTRACT

In one embodiment, a system and a method for inspecting a substance to detect and identify predetermined foreign element(s) in the substance. The foreign element may carry X-ray responding material compositions, emitting X-ray signals in response to primary exciting X-ray or Gamma-ray radiation. The inspection is performed during a relative displacement between the substance and an inspection zone, defined by an overlap region between a solid angle of emission of an X-ray/Gamma-ray source and a solid angle of
(Continued)

detection of X-ray radiation, along a movement path, as the substance moves along the movement path, the detected X-ray radiation includes X-ray response signals from successive portions of the substance propagating towards, through, and out of the overlap region. Measured data indicative of X-ray response signals is analyzed to identify a signal variation pattern over time indicative of a location of at least one foreign element carrying an X-ray responsive marker.

18 Claims, 6 Drawing Sheets

(51) Int. Cl.
  *G01N 23/2206* (2018.01)
  *G01N 23/22* (2018.01)

(52) U.S. Cl.
  CPC ... *G01N 23/2206* (2013.01); *G01N 2223/076* (2013.01); *G01N 2223/0766* (2013.01); *G01N 2223/507* (2013.01); *G01N 2223/652* (2013.01)

(58) Field of Classification Search
  CPC ....... G01N 2223/0766; G01N 23/2208; G01N 23/2209
  USPC ...................................................... 378/44–50
  See application file for complete search history.

(56) References Cited

U.S. PATENT DOCUMENTS

| | | | | |
|---|---|---|---|---|
| 6,177,113 B1* | 1/2001 | Kress | .................... | F28F 19/008 426/232 |
| 7,852,982 B2* | 12/2010 | Saito | .................... | G01N 23/223 378/58 |
| 7,856,081 B2* | 12/2010 | Peschmann | .............. | G01V 5/00 378/57 |
| 7,970,101 B2* | 6/2011 | Sakai | .................... | G01N 23/223 378/45 |
| 8,306,188 B2* | 11/2012 | Klein | ............... | G01N 23/20083 378/53 |
| 8,408,789 B2* | 4/2013 | Takahara | .............. | G01N 23/223 378/63 |
| 8,568,673 B2* | 10/2013 | Kagawa | ................. | B01D 53/64 422/177 |
| 8,611,493 B2* | 12/2013 | Hasegawa | ............ | G01N 23/223 378/44 |
| 8,855,809 B2* | 10/2014 | Spencer | ............... | G01N 23/083 378/53 |
| 8,891,729 B2* | 11/2014 | Matoba | ................ | G01N 23/223 378/53 |
| 9,091,634 B2* | 7/2015 | Miller | .................. | G01N 23/223 |
| 9,201,029 B2* | 12/2015 | Auranen | ............. | G01N 23/223 |
| 9,213,007 B2* | 12/2015 | Matoba | ................ | G01N 23/223 |
| 9,570,265 B1* | 2/2017 | Yun | .......................... | G21K 1/06 |
| 9,594,036 B2* | 3/2017 | Yun | ...................... | G01N 23/223 |
| 9,594,037 B2* | 3/2017 | Mizuno | ..................... | G01T 7/04 |
| 9,606,249 B2* | 3/2017 | Mizuno | ..................... | G01T 7/005 |
| 9,778,214 B2* | 10/2017 | Sako | ..................... | G01N 23/223 |
| 9,829,447 B2* | 11/2017 | Yagi | ..................... | G01N 23/223 |
| 9,897,560 B2* | 2/2018 | Martin | .................. | H01L 23/544 |
| 10,018,748 B2* | 7/2018 | Black | ................. | G01N 33/2823 |
| 10,197,513 B2* | 2/2019 | Kullenberg | .......... | G01N 23/223 |
| 10,207,296 B2* | 2/2019 | Garcia | ...................... | B07C 5/34 |
| 10,393,682 B2* | 8/2019 | Gendreau | ............ | G01N 23/223 |
| 10,416,045 B2* | 9/2019 | Launiere | .................. | C25C 3/34 |
| 10,486,209 B2* | 11/2019 | Wimmer | .............. | G01N 21/718 |
| 10,607,049 B2* | 3/2020 | Grof | ..................... | G06K 7/1099 |
| 10,634,628 B2* | 4/2020 | Kasper | .................. | H01L 21/681 |
| 10,697,906 B2* | 6/2020 | La Belle | .............. | G01N 23/223 |
| 10,697,909 B2* | 6/2020 | Loeffler | ................ | B07C 5/3427 |
| 10,710,119 B2* | 7/2020 | Kumar | ..................... | G06N 3/08 |
| 10,800,315 B2* | 10/2020 | Kanck | ........................ | B60P 3/14 |
| 10,816,488 B2* | 10/2020 | Troadec | ................. | G01N 33/30 |
| 10,823,687 B2* | 11/2020 | Kumar | ................... | G01N 33/15 |
| 10,876,950 B2* | 12/2020 | Mizuno | ............... | G01N 23/223 |
| 10,967,404 B2* | 4/2021 | Grof | ..................... | B07C 5/3412 |
| 11,131,639 B2* | 9/2021 | Mizuno | ............... | G01N 23/223 |
| 11,199,513 B2* | 12/2021 | Koskinen | .............. | G01T 1/2023 |
| 11,215,537 B2* | 1/2022 | Takagi | ................. | G01N 33/287 |
| 11,243,327 B2* | 2/2022 | Scoullar | ............... | G01V 5/0016 |
| 11,293,885 B2* | 4/2022 | Mizuno | .................. | G01N 21/86 |
| 11,360,036 B2* | 6/2022 | Koskinen | ................ | G21K 1/06 |
| 11,442,031 B2* | 9/2022 | Pitta' | ..................... | G01N 23/223 |
| 11,549,896 B2* | 1/2023 | Kinugasa | .............. | G01M 3/02 |
| 11,592,407 B2* | 2/2023 | Segal | .................. | G01N 23/223 |
| 11,680,913 B2* | 6/2023 | Sipilä | ................... | G01N 23/223 378/44 |
| 2013/0034204 A1 | 2/2013 | Matoba et al. | | |
| 2014/0294144 A1 | 10/2014 | Matoba | | |
| 2017/0205362 A1 | 7/2017 | La Belle | | |

FOREIGN PATENT DOCUMENTS

| | | |
|---|---|---|
| JP | S58161854 A | 9/1993 |
| JP | H09230714 A | 9/1997 |
| JP | 2005121468 A | 5/2005 |
| JP | 2007033207 A | 2/2007 |
| JP | 2007078521 A | 3/2007 |
| JP | 2011047741 A | 3/2011 |
| JP | 5553300 B2 | 7/2014 |
| JP | 2016511428 A | 4/2016 |

OTHER PUBLICATIONS

International Search Report with Written Opinion for Application No. PCT/IB2019/001141 dated Aug. 25, 2020, 22 pages.

* cited by examiner

SYSTEM AND METHOD FOR DETECTION AND IDENTIFICATION OF FOREIGN ELEMENTS IN A SUBSTANCE BY X-RAY OR GAMMA-RAY DETECTION AND EMISSION

CROSS-REFERENCE TO RELATED APPLICATIONS

The present application is a national phase entry under 35 U.S.C. § 371 of International Application No. PCT/IB2019/001141 filed Oct. 18, 2019, published in English, which claims priority from U.S. Provisional Patent Application No. 62/747,293 filed on Oct. 18, 2018, all of which are incorporated herein by reference.

TECHNOLOGICAL FIELD

The present invention is in the field of inspection of substances aimed at detection various predetermined foreign elements in the substances. The invention is particularly useful for detection and identification of plastic contaminants in particular plastic fragments originating from plastic products used in agriculture and/or other sources of plastic contamination in fields.

BACKGROUND

The growing use of plastic and polymeric based materials has led to increasing concern over the issue of plastic pollution and plastic contaminants. In particular, use of plastic in agriculture is one of the main sources of plastic pollution in crops and in agricultural produce in general. Plastic products used in agriculture include plastic films and plastic nets used for wrapping and protecting bales of crops (e.g. cotton or hay bales), horticultural twines, shading nets, turf nets, mulching films, and various crop packages. Fragments and shreds of such plastic products may be created during installation of the product in the field (e.g. mulching films and shading nets), during harvesting (for example, in harvesting seed cotton, corn or hay, wherein the harvested crop is packaged in wrapped bales); or further along the supply chain of the crop, for instance during opening and repackaging of a baled crop (e.g. at a cotton gin wherein a bale of wrapped cotton is opened, processed and repackaged into standard compressed bales). In addition, plastic contaminants may originate from other local or incidental sources. Such plastic fragments, whose size may vary widely (from a few $mm^2$ or even less, to tens of $cm^2$) can find their way into the baled or packaged crop. Plastic fragments and shreds within harvested crops may downgrade the quality of the crop and of the final product made from such crops (for example, plastic fragments in cotton may affect the dyeing process of cotton). Moreover, in the case of consumable products, plastic contamination may present a health hazard.

U.S. Pat. No. 6,177,113 discloses a method for processing food product which includes detecting non-metallic equipment fragments or pieces in the food product during processing by employing processing equipment or components fabricated of a material which comprises a non-metallic primary constituent and a detectable particulate metal constituent interspersed substantially throughout the primary constituent such that no substantial adverse effect on the formability, during manufacture, or structural integrity, during use, of the piece part results, and such that a fragment or piece of the composite material is detectable by use of means for detecting the particulate metal constituent.

GENERAL DESCRIPTION

There is a need in the art for a novel approach for detecting and identifying predetermined foreign element(s) in a substance, and preferably in a manner enabling locating parts/fragments of the substance containing those foreign material, e.g. to remove those parts/fragments.

In this connection, it should be noted that foreign materials to be detected are of the kind identifiable by certain characteristic radiation response to incident (reading/exciting) radiation. Such material compositions having characteristic radiation response may be constituted by a foreign element naturally existing/developing in a certain substance as a result of preceding effects/events to which the substance might have been exposed/subjected to, e.g. material composition resulting from a decay and degradation of a product. Alternatively, such material composition having characteristic radiation response may be constituted by a predetermined marker intentionally embedded in a foreign element (e.g. plastic) in order to identify/classify said foreign element (for example in association with the manufacturer of said element), which might be embedded in fragments of the substance (crop) as a result of preceding processes/events.

Various foreign elements, such as plastics, carry their specific markers intentionally embedded in the element (on a surface or in a bulk) in a manner enabling identification of the marker, and accordingly the foreign element, by detection of the marker's unique/specific characteristic radiation response (radiation signature). Suitable markers, marking techniques and markers' identification techniques, based on X-ray or Gamma-ray radiation, have been developed and are described for example in WO16157185, WO18055625, WO18069917, WO18051353, WO17221246, WO17175219, all assigned to the assignee of the present application and being incorporated herein by reference.

The present invention provides a novel inspection system and method, which allows for automatic or semi-automatic inspection of a substance to detect, identify and preferably also locate in said substance fragments thereof containing certain predetermined foreign element(s). The invention provides for such inspection during the substance progression on a production line.

Thus, according to one broad aspect of the invention, it provides a system for detecting and identifying at least one predetermined foreign element in a substance, the system comprising:

a measurement device comprising: a radiation source assembly comprising at least one source of X-ray or Gamma-ray radiation, each source being configured to generate X-ray or Gamma-ray radiation having predetermined properties and a predetermined solid angle of radiation emission to excite a portion of the substance located in a region within said predetermined solid angle to cause an X-ray response of said portion; and a detection assembly comprising at least one detector having a solid angle of radiation detection overlapping with said solid angle of radiation emission, each detector being configured and operable to detect X-ray radiation propagating within the solid angle of radiation detection and generate measured data indicative of detected X-ray radiation; the measurement device being configured and operable such that the X-ray radiation being detected during a relative displacement between the substance and at least one of the radiation source assembly and the detection assembly along a movement path is indicative of a time variation of the X-ray response of the substance; and a control unit configured and operable for data communication with said detection assembly to receive and analyze the measured data, the control unit comprising a signal processor configured and operable to identify in said measured data a pattern of a signal variation over time indicative of a location of at least one foreign element carrying an X-ray responsive marker in said substance.

The system may or may not include a flow line arrangement configured and operable to define the movement path. This may, for example, be a pipe-like device through which the substance can flow with respect to stationary or moving radiation source and detector; or may be a support platform (e.g. conveyor) for supporting and moving the substance with respect to stationary or moving radiation source and detector.

As indicated above, the present invention is particularly useful for solving a problem of identifying plastic fragments within a bale or a package of crop, and is therefore described below with respect to this specific application. It should, however be noted that the principles of the invention are not limited to this specific application.

The invention provides for inspecting the substance, e.g. crop, during processing (for example, on a conveyor belt or in a pipe), which is a challenging task, in particular with respect to small fragments, of a few $cm^2$ in size or less. Moreover, identifying the source of the plastic fragments, that is, identifying the type of product or the particular product from which the fragments originated, may have significant advantages, as one would be able to deal with the plastic contamination source and/or assign responsibility for such contamination.

Preferably, the movement path passes through (its axis intersects with) an overlap region between the solid angle of radiation detection and the solid angle of radiation emission.

As indicated above, the flow line arrangement may be provided comprising a support platform for supporting the substance and moving the substance with respect to the at least one of the radiation source assembly and the radiation detection assembly.

In some embodiments, the flow line arrangement comprises a translation assembly configured and operable for translating at least one of the radiation source assembly and the radiation detection assembly with respect to the movement path. The translation assembly may be configured and operable for translating both the radiation source assembly and the detection assembly with respect to the movement path. The translation assembly may perform simultaneous translation of the radiation source assembly and the detection assembly such that their solid angles of emission and detection are oriented towards two opposite lateral sides of the movement path.

The signal processor may be configured and operable to integrate the measured data indicative of the X-ray response being detected over time while the foreign element is being moved through the overlap region.

In some embodiments, the source assembly and the detection assembly are oriented with respect to the movement path such that their solid angles of radiation emission and detection oppose a direction of movement of the substance along the movement path, such that, when the substance moves through an inspection zone defined by (aligned with) the overlap region, a distance between the substance and each of the source and detector is being reduced. This arrangement of the inspection mode/scheme provides that the pattern of the signal variation over time is characterized by a non-symmetric characteristic signal peak indicative of the location of the at least one foreign element and having a moderate rise of the signal intensity when the distance is being reduced and a sharp intensity fall when the location of the at least one foreign element exits the overlap region. This enables to accurately identify the location of the at least one foreign element along at least one dimension.

As described above, the signal processor may be configured and operable to integrate the measured data indicative of the X-ray response being detected over time while the foreign element is being moved through the overlap region. This would emphasize the non-symmetric characteristic of the signal peak in the time pattern of the signal variation.

In some embodiments, the relative displacement defines the movement path of substantially linear geometry.

Alternatively, or additionally, the relative displacement defines the curvilinear movement path having at least one curved portion aligned with a boundary of said overlap region.

In some embodiments, the source assembly and the detection assembly are accommodated at opposite lateral sides of the movement path, thereby yielding reduced variation in detected signal intensity of the X-ray response of a responding foreign element, irrespective of a lateral location of the responding foreign element in a bulk of said substance while in said overlap region. The accommodation may be such that the exciting radiation and the X-ray response being detected vary with a distance from the radiation source and radiation detector.

The signal processor may be configured and operable to identify the foreign element(s) by analyzing the detected X-ray response signal over a database storing X-ray signatures corresponding to multiple known X-ray responsive markers.

In some embodiments, the foreign element(s) to be identified comprise(s) one or more plastic elements carrying one or more X-ray responsive markers. The signal processor may be configured and operable to process the measured data and generate data indicative of quantity of plastic elements within at least a portion of the substance.

In some embodiments, the radiation source assembly comprises at least two sources of the X-ray or Gamma-ray radiation. The configuration may be such that each radiation source has the solid angle of emission oriented with respect to the movement path to irradiate a different side surface of the substance, and the detection assembly comprises the at least one X-ray detector with the solid angle of detection oriented to detect the X-ray response signals propagating from a top surface of the substance.

In some embodiments, the detection assembly comprises at least two detectors whose solid angles of detection are oriented with respect to the movement path to receive the X-ray response signals propagating from two opposite side surfaces of the substance, and the solid angle of emission of the at least one source of the X-ray or Gamma-ray radiation is oriented to irradiate a top surface of the substance.

In some embodiments, the radiation source assembly and the detection assembly are accommodated with respect to the movement path such that the solid angles of emission and detection are oriented towards two different surfaces of the substance.

As described above, the movement path may be configured as or may include the curvilinear path. For example, the substance flows through a pipe-bend.

According to another broad aspect of the invention, it provides a method for inspecting a substance to detect and identify at least one predetermined foreign element in the substance, the method comprising: providing a relative displacement between a substance being inspected and an inspection zone, defined by an overlap region between a solid angle of emission of a source of X-ray or Gamma-ray radiation and a solid angle of detection of X-ray radiation detector, along a predetermined movement path, such that during the substance movement along said movement path, the detected X-ray radiation includes X-ray response signals from successive portions of the substance propagating towards, through, and out of said overlap region; and receiving and analyzing the X-ray response signals to identify, in said detected X-ray radiation, a pattern of a signal variation over time indicative of a location of at least one foreign element carrying an X-ray responsive marker in said substance.

As indicated above, in some embodiments, the present invention provides a novel technique for identifying plastic fragments within a bale, a package or a stack of crop, wherein the crop is either in a stationary state or moving (for example, on a conveyor belt or a pipe during processing). More specifically, the inspection technique of the present invention is based on identification of one or more markers embedded within or applied to a surface of one or more plastic products, which are potential source of plastic contaminants (e.g. plastic fragments) found in crops, such as wrapping films or nets for bales of crops. The marker(s) can be detected by the system of the present invention by employing X-Ray Fluorescence (XRF) analysis described for example in the above-listed patent publications for the inventions developed by the inventors of the present invention. The detectable X-ray signal has an energy of at least 0.1 KeV. Namely, the one or more markers, embedded within, or applied to a plastic product, may emit an X-ray signal in response to incident (primary) X-ray or Gamma-ray radiation. The X-ray signal emitted by the one or more markers (hereinafter "response signals") includes one or more features corresponding to a characteristic radiation response of a specific marker and thus identifying said markers. The response signal can therefore be utilized as a unique radiation signature (at times referred to XRF signature) identifying the particular foreign element (plastic product). Additionally, the XRF signature can be utilized to encode additional information, such as the type of the foreign element/product, and/or the manufacturer of the product, the date of manufacture or delivery, the end-user of the product, and so on. Marking of the foreign elements, such as plastic products, detectable and identifiable by the technique of the present invention may for example be of the type used for anti-counterfeit and brand protection, as well as for track & trace and supply-chain management purposes.

The particular marker(s) identified may be used to identify one or more sources of plastic pollution found in crops. For example, plastic fragments which may be found in a processed bale of crop may come from a plastic film wrapping bales of harvested cotton, plastic bands used in a gin for packaging a compressed processed bale, or from other local or incidental sources in the region of the cotton field. Marking the plastic wrapping films and inspecting the cotton during processing in the gin or the processed bale would enable one to determine whether the plastic wrapping is responsible for the plastic fragments within the processed bales, or not. Marking of the plastic wrapping film may also be used to identify the manufacturer of the wrap. For example, it may distinguish between a marked higher quality product designed to avoid the potential of plastic contamination, and an unmarked lower quality product.

The technique of the present invention allows to detect and identify marked fragments and shreds of foreign elements (e.g. plastic) whose external surface size may be no larger than tens of $mm^2$ and whose thickness may be no larger than tens of microns. Moreover, the technique of the present invention enables the detection and identification of marked fragments of foreign element (e.g. plastic) which are located within a substance, such as a bale, package or stack of crop, which may be stationary or moving (e.g. on a conveyor belt or in a pipe). Namely, foreign elements (plastic fragments) which are hidden from view and located inside the substance (e.g. crops), can be detected and identified by the technique of the present invention. It should be understood that, as the foreign elements (plastic fragments) may be of small size and completely hidden from view, their detection by optical methods and instruments is infeasible. Furthermore, considering that different products (foreign elements) are marked with different markers, the technique of the present invention allows one to identify and distinguish between different products (for instance, an original and a counterfeit product). In an example, the technique of the present invention may be used for distinguishing and identifying plastic products according to their environmental footprint. For instance, three known categories of plastic products, biodegradable, bio-based (products derived from renewable biomass sources which are not necessarily biodegradable) and 'regular' (non-biodegradable or bio-based) plastic materials may be marked with one, two, or all of the three categories of products, each with a different marker(s).

The marker(s) detectable/identifiable by the present invention may by incorporated within a foreign element (plastic product) during production of the foreign element by various techniques, for example extrusion, reactive extrusion, molding, injection and other forming methods. The marker(s) may be added to the plastic in an extrusion process (for example via a main resin feedstock or a secondary feeder) in the form of resin, pellets, powder, or in liquid form. Furthermore, the marker(s) may be prepared and included in pellets containing additional additives.

In a different example, the marker(s) may be applied to the plastic products after production by, using non-limiting techniques such as stamping, brushing, spaying, air brushing, and printing.

Thus, in some embodiments of the present invention, it provides a method for detecting and identifying online plastic fragments and shreds within a stack or a bulk of crop on a conveyor belt. The inspection system of the present invention can be installed, for instance, in a processing facility detecting plastic contaminants within a bulk of crop, as it is being processed (i.e. progressing on a production line). In a particular example, it may be installed in a cotton gin wherein harvested cotton (often packaged in wrapped bales) is processed for separating the fibers from the seeds and packed in compressed bales for storage and/or shipping. In a different example, the system of the present invention may be installed in facilities for processing consumable crops such as grains, cereals, vegetables and fruits. In a particular example, the system may be installed in a mill detecting and identifying plastic fragments within the grains as it is being processed (for instance as the grains undergo various sorting processes).

As described above, according to the invention, inspection of the substance to detect and identify foreign elements (e.g. plastic fragments and shreds) throughout the cross section of the substance (e.g. bulk of crops) is performed during relative displacement between the substance and the radiation source and/or radiation detector, e.g. during the substance progression on a conveyor belt (the direction of progression being perpendicular to the cross section of the substance), The exciting X-ray or Gamma-ray radiation preferably irradiates the entire cross section of the substance (bulk of crop). Once the exciting radiation from the radiation source assembly reaches the marked foreign element (plastic fragments), the response signal emitted by the marker(s) on or in the foreign element should reach at least one detector of the detection assembly so that the XRF signature of the marker/foreign element can be properly read/detected. The radiation source and detection assemblies are appropriately configured and operable to excite the marker(s) in a manner enabling emission of the response signal from the marker(s) of high enough frequency range (energy range) and power (number of photons) capable at crossing the substance (bulk of crop) and be detectable, i.e. to avoid attenuation of the response signal by the substance bulk to such a level that the number of counts at one or more detectors does not provide a reliable identification of the XRF signature. In order to be able to provide effective excitation, the primary radiation is preferably of a frequency range which is at least as high as the range of frequencies emitted by the marker(s), and preferably 2-4 times higher. The present invention is advantageously suitable for detecting foreign elements within organic substances (e.g. crops), which, due to their relatively light weight, practically do not attenuate the X-ray radiation from the source and the X-ray radiation emitted from foreign elements in the substance, as such radiation progresses inside the substance, as compared to that of heavier materials.

In some embodiments, the source assembly is operable to continuously emit X-rays towards the substance during the relative displacement along the movement path, and the detector continuously detects X-ray signals emitted by the substance and collects the data (i.e. counts/integrates) in time bins (the duration of which may vary from less than a millisecond to a few seconds). The signal processor operates to identify within the spectrum of the detected signal, one or more features (XRF-signatures) corresponding to the marker (s). Once the XRF-signature of at least one marker is identified, the processor provides an indication identifying the foreign elements (plastic products) or types of foreign elements corresponding to the marker and any other information that may correspond to the particular XRF-signature. The processor may also provide an indication as to the quantity (measured by weight or volume) of the foreign element (plastic) contaminants in a section (a cross section of the bulk times the distance corresponding to one or more time bins) of the substance continuously moving on the conveyor belt. Additionally, the processor indicates the location of the identified foreign element in the substance (plastic fragments within the bulk of crop, i.e. a section of the bulk where plastic contaminants are located.

In order to provide measured data with regard to the fragments of the foreign element in the substance, which is precise in terms of quantity and location, and which is carried out in a short time, the system of the present invention is configured to collect as much data (namely counts from the marked foreign element) per time unit as possible. The level of counts per second originating from the marked foreign element depends on a plurality of factors including two or more of the following: the overall quantity of marked foreign element within the section of the substance being excited by the source assembly and detected by the detector; the marker material which determines the frequency range of the XRF-signatures of the markers; the power and frequency of the exciting radiation; the cross-sectional dimension of the substance bulk and its density (i.e. mass per unit volume); and the geometrical configuration of the source-target-detector (i.e. the orientation of each of the solid angles of radiation and detection with respect to the target (e.g. the particular foreign element whose marker emits a response signal), the size of the solid angles (i.e. apertures of the source assembly and detection assembly), distances from each of the source assembly and detection assembly to the target (distances within the substance bulk and outside the bulk).

As described above, in some embodiments, the source assembly and the detection assembly are positioned on opposite sides of the movement path such that their solid angles are directed towards opposite sides of the substance during movement along the movement path (e.g. conveyor belt). Such a configuration has an advantage that foreign elements located within the substance on the side which is opposite to the source assembly (and therefore at a greater distance from it) are closer to the detection assembly and vice versa (foreign elements which are close to the source assembly are distant from the detection assembly), such that the sum distance from the source assembly to the foreign element and from the foreign element to the detection assembly, is similar for all foreign elements throughout a cross section of the substance bulk (or at least are not very different for different foreign elements). Consequently, if the exciting radiation beam propagating from the source assembly to a foreign element is significantly attenuated by the distance, the radiation response signal emitted by the foreign element towards the detection assembly will not be attenuated (and vice versa), thus contributing to the accuracy of measurement of the quantity of marked foreign element in a section of the substance bulk.

In some embodiments, the detection assembly and the source assembly are not positioned on the same axis exactly opposite each other (such that the solid angles (apertures) of the source assembly and detection assembly are exactly facing each other). For example, the detection assembly may be slightly translated from the axis defined by the position of the source assembly and the direction of its solid angle, in order to minimize the amount of primary exciting radiation arriving directly from the source assembly to the detection assembly.

Alternatively, the detection assembly may be positioned above a substance during the movement along the movement path and the source assembly is accommodated at the side of the substance at a relatively large angle with respect to the detection assembly.

In additional embodiments, two radiation sources are provided being positioned on opposite sides of the movement path (opposite sides of the substance on a conveyor belt or a continuous track) and a single detector is positioned above the movement path (above the top surface of the bulk. In further embodiments, two detectors are positioned on opposite sides of the movement path (opposite sides of the substance on a conveyor belt), and a single radiation source is positioned above the movement path (above the top surface of the substance).

As also described above, in another embodiment, the substance being inspected moves in a pipe (for example cotton in a cotton gin). The radiation source assembly and/or the detection assembly are preferably accommodated at a pipe bend region, and may be installed in the pipe bend. The source assembly emits the primary exciting X-ray or Gamma-ray beam towards the substance while approaching the pipe bend region during movement along the pipe in its general propagation direction (namely, the exciting beam propagates in a direction generally opposite to the direction of movement of the substance). The solid angle of detection is oriented towards the moving substance, such that a backscattered response signal propagates from the excited region of the substance). Such a configuration may contribute to the accuracy of the detection and identification of the marked foreign elements, enabling better estimations of the quantities of foreign elements' contaminants in the substance since all fragments of the marked foreign element(s) move with the substance along the movement path in a direction towards the source and detection assemblies and detector, avoiding a situation where both primary radiation and the response signal from different portions of the substance are attenuated to very different levels, due to different paths of the radiation propagation in the substance.

As also mentioned above, in some embodiments of the present invention, the substance being inspected is, in general, stationary, and the source assembly and the detection assembly scan the substance while moving in parallel along the movement path such that their solid angles are oriented towards opposite surfaces of the substance.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which.

DETAILED DESCRIPTION OF EMBODIMENTS

Figure 1:
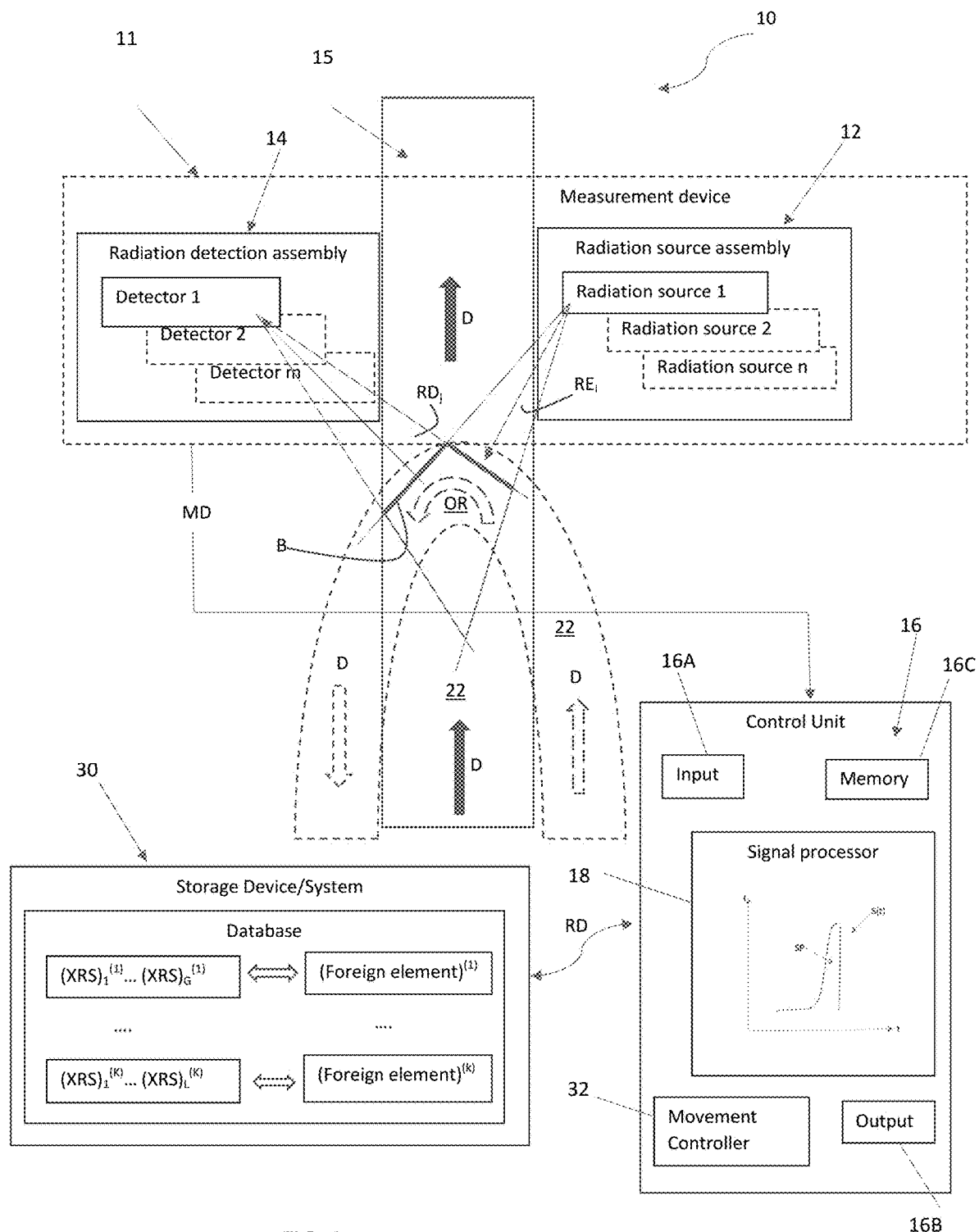
FIG. 1 is a block diagram of a system of the invention for inspecting a substance and detecting and identifying predetermined foreign element(s) in the substance.

Referring to FIG. 1, there is illustrated, by way of a block diagram, a system 10 configured and operable according to the principles of the invention for inspecting a substance and detecting and identifying predetermined foreign element(s) in the substance. The foreign element to be detected and identified by the system 10 is a so-called "marked" foreign element whose marking(s) has/have characteristic radiation response(s) to predetermined X-Ray or Gamma-ray radiation, which is/are previously determined and stored in a database accessible by the system 10 (via any suitable known communication technique).

The system 10 includes such main constructional and functional parts as a measurement device 11, and a control unit 16. The measurement device 11 includes a radiation source assembly 12 comprising one or more sources of X-ray or Gamma-ray radiation and a radiation detection assembly 14 comprising one or more detectors configured and operable to detect X-ray radiation. Each i-th radiation source (i=1, . . . n) has a predetermined solid angle of radiation emission $RE_i$ to excite a portion of the substance located in a region within this solid angle $RE_i$. Similarly, each j-th radiation detector (j=1, . . . m) has a solid angle of radiation detection $RD_j$.

It should be understood that a solid angle of radiation propagation is characterized by a general ray propagation direction (being direction from the source and direction towards the detector, respectively) and the angular shape and size (i.e. the shape and size of the field of view of the source and detector, respectively). The solid angle of radiation emission, which defines/determines the volume of the irradiated media/space and its location with respect to the source assembly (i.e. general direction of radiation propagation) is determined by the aperture of the source and possibly also a collimator used in the source. It should be noted that the cross-section of the solid angle may be of any suitable geometry/shape and dimensions, which may or may not be equal along the two perpendicular axis (so-called symmetric or non-symmetrical shape), for example the cross section may be circular, oval-like (e.g. elliptical), or polygonal. The irradiated volume would be of the corresponding shape. Similarly, a volume of space from which a signal can reach the detector is determined by the solid angle of radiation detection, which in turn is determined by an aperture and possibly a collimator used in the detector, and this "readable" volume may be symmetric on non-symmetric in the meaning described above. In this connection, it should also be understood that an actual volume of the region of interest being "read" by the detector is defined by an overlap region between the solid angles of emission and detection within the region of interest, as will be described more specifically further below.

It should also be understood that if more than one radiation source is used and more than one detector is used, the number of radiation sources may or may not be equal to the number of detectors.

The configuration of the measurement device 11 (i.e. the orientation of the solid angle(s) of emission and the solid angle(s) of detection) is such that there exists at least one overlap region OR between the solid angles of emission and detection. The overlap region OR actually presents an effective inspection zone. It should also be understood that the radiation source assembly 12 and the radiation detection assembly 14 are appropriately configured to, respectively, generate and be able to detect the X-ray radiation of certain frequencies in accordance with the foreign materials (i.e. markers) to be detected, i.e. radiation capable of exciting certain material compositions to induce X-ray response signals that can be detected by the detection assembly. The radiation detection assembly 14 detects the X-ray response signals and generates measured data MD indicative of said X-ray response.

The system 10 of the invention is configured such that measurement device 11 performs the inspection session(s) of the substance during a relative displacement between the substance and at least one of the radiation source assembly 12 and the radiation detection assembly 14 along a movement path 22. With this configuration, the X-ray response signals are being detected during the relative displacement along the movement path. More specifically, the relative displacement is between the substance and the overlap region OR between the solid angle of radiation detection $RD_j$ and the solid angle of radiation emission $RE_i$. The relative displacement provides a movement of a substance (not shown here) in a direction D towards, through and away of the overlap region OR. Thus, the successive regions/portions of the substance successively passing through the overlap region OR are scanned during the movement. As schematically shown in the figure, and will be exemplified and described more specifically further below, the movement path 22 may be a substantially linear path at least in its portion passing through the overlap region, or as shown by dashed curves, the movement path may be a curvilinear path or have a curved portion aligned with a boundary B of the overlap region OR.

The system 10 may thus be associated with (e.g. may include as its constructional part or may be used with) a flow line arrangement 15, configured to support the substance in a manner allowing its flow with respect to one or more of the radiation source(s) and radiation detector(s), and/or to translate one or more of the radiation source(s) and radiation detector(s) with respect to the substance.

The control unit 16 is generally a computer device/system having such main functional utilities as data input and output 16A and 16B, memory 16C, and a single processor 18. The control unit 16 is configured and operable for data communication with the detection assembly 14 to receive and analyze the measured data MD.

It should be understood that, generally, the invention is aimed at detecting the existence of and preferably also location of one or more foreign elements in a substance, in order to "classify" or "sort" the substance as carrying such foreign elements and/or in order to enable removal of the foreign elements from the substance. The foreign elements are of the kind providing X-ray response to primary exciting X-ray or Gamma-ray radiation. Typically, the X-ray response is that generated by specific markers embedded in the foreign elements. The case may be such that detection of the existence of any such "marked" foreign element in the substance is enough to classify or sort the substance; or such that the detection and location of any such "marked" foreign element in the substance is enough; or may be such that identification of the marking and accordingly the foreign element is required or, even more, the detection itself is possible only with respect to identifiable foreign elements.

Hence, in some embodiments, the signal processor 18 is also configured to (selectively) access a storage device 30 which may be constituted by the internal memory 16C or may be an external storage device accessible via a communication network in which predetermined reference data RD is stored comprising data indicative of various X-ray signatures of various markers in association with respective foreign elements. Generally speaking, each k-th foreign element (k=1, ..., K) in the database has a number of its associated one or more characteristic X-ray signatures of respective one or more markers. For simplicity, in the non-limiting example of the figure, one of the foreign elements, (Foreign element)$^{(1)}$, has a number g (g=1, ... G) of its associated characteristic X-ray signatures, $(XRS)_1^{(1)}$ ... $(XRS)_G^{(1)}$; and another foreign element, (Foreign element)$^{(k)}$, has a number l (l=1, ... L) of its associated characteristic X-ray signatures, $(XRS)_1^{(l)}$ ... $(XRS)_L^{(l)}$; where such numbers L and G of the X-ray signatures associated with different foreign elements may be equal or not. The signal processor 18 is configured and operable to identify in the measured data MD a pattern of an X-ray response signal variation over time, which is indicative of a location of at least one foreign element carrying a predetermined X-ray responsive marker.

More specifically, the signal processor 18 includes an identifier module/utility configured and operable to identify in the measured data, being collected during the movement, the X-ray response signal indicative of the existence of some X-ray responding element in the substance (in case the substance is otherwise not X-ray responding at all) or the X-ray response signal corresponding to the foreign element whose associated reference data is stored in the database. Also preferably provided in the signal processor is a locating module/utility configured and operable to identify the pattern of the X-ray response signal variation over time and determine the location of the respective foreign element. To this end, the control unit 18 may also include a movement controller 32 providing data indicative of a motion pattern of the substance with respect to the overlap region.

As will be exemplified and described more specifically further below, the system is preferably configured such that the solid angles of radiation emission and detection $RE_i$ and $ED_j$ are oriented with respect to the movement path 22 in a manner opposing the direction D of movement of the substance along the movement path 22. With this configuration, when the substance moves towards the overlap region OR, a distance d between the substance and each of the source and detector is being continuously reduced, and starts increasing when the substance moves away from the overlap region. As schematically shown in the figure, this results in that the pattern of the X-ray response signal variation over time, S(t), has a non-symmetric characteristic signal (intensity vs. time) peak SP indicative of the location of the responding marker (responding foreign element). It should be understood that this pattern has a moderate rise of the signal intensity when the distance d is being reduced and a sharp intensity fall when the location of the responding foreign element exits the overlap region OR. This enables accurate identification of the location of the responding foreign element along at least one dimension. As will also be described further below, the signal processor 18 is preferably configured and operable to integrate the measured data (counts) indicative of the X-ray response being detected over time while the substance (and thus the foreign element) is being moved through the overlap region OR, thereby emphasizing the non-symmetric characteristic of the signal peak.

It should be understood, although not specifically shown, that the flow line arrangement 15 may also include one or more drive units associated with one or more of the substance support platform (e.g. conveyor), the radiation source(s) and the detector(s) for implementing a controllable relative displacement along the movement path.

The following is the description of some specific but non limiting examples of the configuration/implementation and operation of the above-described system of the invention. In these non limiting examples, the inspection system is described as being used for detecting and identifying plastic contaminants within crops.

Figure 2A:
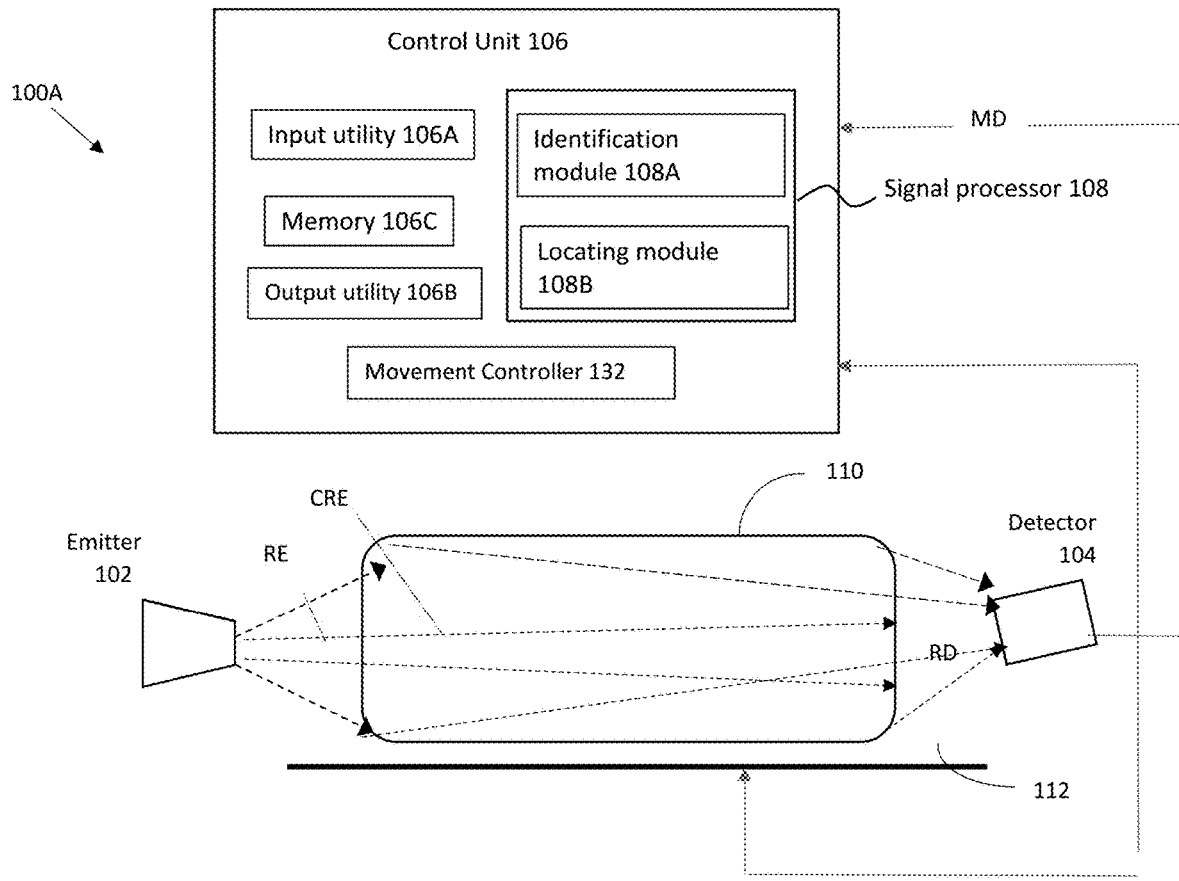
FIGS. 2A and 2B show an exemplary configuration of the system of FIG. 1.
Figure 2B:
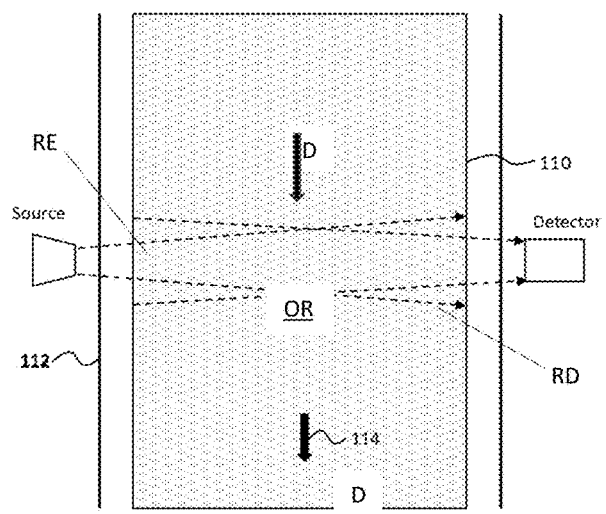

Reference is made to FIGS. 2A and 2B which schematically illustrate an inspection system 100A, which is configured generally similar to the above-described system 10, namely includes: a measurement device including a radiation source assembly (emitter) 102 and a detection assembly (detector) 104; and a control unit 106. The control unit 106 includes input and output utilities 106A and 106B, memory 106C and signal processor 108, and a movement controller 132. The signal processor 108 includes an identification module 108A and a locating module 108B configured and operable as described above. The signal processor is configured as described above to process and analyze measured data MD provided by the detector, by utilizing reference data obtained from a database (e.g. in an external storage device), which is not specifically shown here. FIGS. 2A and 2B show, respectively, the schematic front view and schematic top view of radiation propagation scheme with respect to the movement path. The system 100A is used with a flow line arrangement, which is exemplified here as a continuous track 112 (constituting a substance support platform) defining a movement path.

Thus, the system 100A includes the radiation source assembly 102 configured for emitting X-ray or Gamma-ray radiation towards a stack or bulk of crop 110 (constituting a substance) moving on a continuous track 112 such as a conveyor belt (constituting a substance' support platform), and the X-ray radiation detector 104 for detecting X-ray response signals, emitted from plastic contaminants that might be contained in the bulk of crop, and generating measured data MD indicative of the detected signals. The signal processor 106, which is in communication with the detector 104, is configured to detect and identify marked plastic contaminants within the bulk of crop. The marked plastic contaminants may be fragments and/or shreds of marked plastic products used during cultivation, harvesting, and processing of the crops. For example, agricultural products such as plastic wraps or nets used for wrapping bales of cotton, hay, or straw, shading nets, mulching films, and various crop packages. Such plastic products, which are likely sources for plastic contamination in crops, are marked by marker(s) comprising one or more markers identifiable according to their characteristic XRF signature (namely, the X-ray response signal to predetermined exciting radiation of each such marker includes one or more unique features corresponding to the marker).

The marker(s) may be embedded in the plastic products during production by methods such as extrusion, molding, injection, casting and other forming methods. Since the marked plastic products are commonly agricultural products installed in the field, the marker(s) embedded within the product is to be robust and able to withstand harsh weather conditions. Moreover, the marker(s) affect the robustness of the plastic products and their ability to withstand varying environmental conditions, or any of its properties such as strength, elasticity, UV stability, waterproofing capability, appearance, and so on. Additionally, the marker(s) do not negatively affect the plastic products' biodegradability. In an example, the marker(s) is/are embedded within or applied to the plastic product in a concentration of less than 10,000 ppm or less than 5000 ppm. Particular examples of marker(s) for polymers which can be detected and identified by the system of the present invention are described in the above-indicated patent publication WO 2018/069917 assigned to the assignee of the present application.

Such plastic products may tear and/or disintegrate, forming fragments or shreds by various causes. For example, pieces of products installed in the field, such as shading nets or mulching films, may disintegrate due to UV radiation from the sun, plastic shreds may be created when bale wraps of nets are cut and opened before processing (e.g. wrapped cotton bales in the gin). Plastic fragments and shreds from agricultural products, as well as from local and/or incidental sources, may find their way into the processed crop and may appear throughout the bulk on the continuous track.

The inspection system 100A is configured to detect and identify plastic fragments located anywhere within the bulk of crop 110 moving on the continuous track 112 (constituting substance' support platform) along the movement path. It should be understood that the continuous track 112 actually presents/defines a movement path resulting from a relative displacement between the bulk of crop 110 and the effective inspection zone (overlap region between the solid angles of emission and detection). As described above, such relative displacement may be achieved by actual movement of either one or more of the emitter 102, detector 104, and substance support platform.

In order to identify plastic fragments, the radiation source assembly 102 emits exciting X-ray or Gamma-ray radiation towards the bulk of crop 110 on the continuous track 112. Marked plastic fragments, when being irradiated by such exciting radiation (with high enough power and frequency) in region(s)/location(s) of the marker(s) within, or on the plastic, emits X-ray response signals, which pass through the bulk of crop and some distance in air and reach the detector 104. The bulk of crop unavoidably attenuates the response signal passing therethrough. Therefore, in order for the response signal to reach the detector with sufficient intensity to facilitate accurate measurement, it should be of (i) sufficient intensity (i.e. a sufficient number of photons is to be emitted by the markers); and (ii) sufficient energy (i.e. each photon should be of sufficient energy (or frequency)). The higher the energy of the photons, the smaller the absorption of the signal in the crop material (which is an organic, and therefore light material). The radiation source and detector are appropriately configured such that the primary radiation emitted by the emitter is capable of exciting the crop material to cause the response signal from a marker (i.e. the XRF-signature associated with the marker) detectable by the detector. As described above, to this end, the frequency of the exciting radiation is at least as high as the frequency range of the response signal of the particular marker which is to be detected. Preferably, the frequency of the exciting radiation from the emitter assembly is two to three times higher than the expected/searched for response signal of the particular marker. In an example, the XRF-signatures of the one or more markers are of an energy range between 15 KeV and 90 KeV, and consequently the radiation emitted by the emitter assembly is in a range from 30 KeV to 270 KeV. The energy range of the XRF-signatures of the markers may be between 35 KeV and 80 KeV, and consequently the radiation emitted by the emitter assembly is in a range from 70 KeV to 240 KeV. In an example, the markers may be materials with response signals in the above energy ranges. For instance, the markers may include any one or more of the following elements: Zr, Nb, Mo, Pd, Ag, Cd, In, Sn, Sb, Te I.

The attenuation of both the exciting radiation propagating from the emitter assembly to the marker location in the substance (crop bulk) and the response signal propagating from the marker location to the detector depends on the size of a cross section of the substance media (bulk of crop) 110 and its density. Due to attenuation of the signals in the crop which affects the amount of data collected by the detector in unit time, the response signal is to be measured with efficiency, collecting as much data in a time unit as possible. In particular, the measurement mode/scheme is configured to enable detection of signals from marked plastic fragments anywhere within the bulk of crop 110 including plastic fragments which are located on the far end of the bulk relative to the detector 104 and to the emitter assembly 102. It should be noted that in a configuration wherein both the emitter assembly 102 and the detector assembly 104 are positioned on the same side of the movement path (i.e. on the same side of the bulk of crop 110), plastic fragments which are located on the opposite side of the bulk might be difficult to detect, since the exciting radiation from the emitter assembly is attenuated by the relatively long path within the bulk of crop, resulting in a weaker response signal which is further attenuated by the relatively long path to the detector.

In the exemplary system 100A of the present invention, emitter assembly 102 and detector assembly 104 are positioned on opposite sides of the movement path 112 (on opposite sides of the bulk of crop 110), such that plastic fragments which are located within the crop bulk on the far end of the crop bulk relative to the emitter assembly 102 are not too distant from the detector 104. Also, in this example, the detector 104 is located in a position that slightly deviates from the central ray CRE of the solid angle of radiation emission RE (the center of the emitter's aperture). Hence, as better seen in FIG. 2A, the detector and emitter may be accommodated such that the solid angle of detection is not exactly opposite to the solid angle of emission, but rather the detector's aperture (defining the solid angle) is oriented such that its central axis deviates from the central axis of the emission aperture in order to minimize the amount of primary radiation arriving directly from the emitter assembly 102 to the detector assembly 104.

The emitter assembly 102 directs X-ray or Gamma-ray radiation towards a section/portion of the bulk of crop 110 (as shown in FIG. 2B). Namely, the primary exciting radiation from the emitter assembly irradiates not the entire cross section of the bulk 110 but only a section/portion thereof which arrives to and passes through the overlap region OR (inspection zone), during the crop bulk movement in the direction D along the movement path (continuous track) 112. The detector 104 receives a sequence of successively generated X-ray response signals from sections/portions of the crop bulk successively passing through the overlap region. The size of the section/portion of the crop bulk being excitable is generally determined by the aperture of the radiation source, and a part of said section/portion of the crop bulk emitting the response signal which is detected by the detector is defined by the intersection of solid angles of emission and detection, i.e. the overlap region OR.

As described above, the signal processor 106 includes data input utility 106A (which may include an appropriate communication module) for receiving the measured data indicative of the detected X-ray response signals, memory (i.e. non-volatile computer readable medium) 106C for storing database configured as described above for storing preselected data indicative of marking signatures of marked plastic products and of the intensity of the response signal, and the signal processor utility 108 adapted for identifying marked plastic products in the crops and providing indication as to their position on the continuous track. The signal processor utility 108 may further include the identification module 108A adapted for analyzing data collected from the detector 104 and identifying XRF signatures of the various marked products found in the bulk of crop 110, and the locating module 108B adapted for computing and providing indication on the location of plastic fragments in the bulk 110 Based on data provided by the movement controller.

The emitter assembly 102 and the detector assembly 104 may operate continuously for emitting and detecting radiation. The X-ray response signals (counts and/or counts per second in a plurality of energy ranges) are collected and stored in time bins. That is, counts of the detected signals, corresponding to each of a plurality of energy bands emitted by the substance for a preselected duration of time $T_c$, as the substance being inspected (e.g. bulk of crop) is displaced with respect to the overlap region along the movement path (e.g. advances on the continuous track 112), are collected, and corresponding measured data is generated and stored in the memory 106C. Signal processor 108 analyzes measured data pieces of the measured data collected in successive time bin, and as the substance (bulk of crop) is being moved (advances on the continuous track), the particular time bin and its corresponding measured data piece is related to a section of a length $l=T_c \times v$, wherein v is the velocity of movement. Signal processor utility 108 is configured to identify the measured data piece corresponding to the time bin and its corresponding section/portion in the substance 110 for the detected X-ray response signals corresponding to the XRF signature(s) of one or more marked foreign elements (plastic products). The signal processor utility 108 may also assess the quantity (in volume or weight) of plastic fragments (either the overall quantity or the quantity of each marked product or type of products) found in each section/portion of the bulk of crop 110. In an example, the inspection system 100A identifies sections/portions of the crop contaminated with marked plastic fragments, distinguishing between biodegradable, bio-based, and 'regular' non-degradable or bio-based plastic fragments.

It should be noted that the signal processor used in the system of the present invention may be adapted for utilizing advanced methods for amplifying, filtering and/or enhancing the detected XRF response signals. For example, such methods are described in the above-indicated patent publication WO 2016/157185 assigned to the assignee of the present application and incorporated herein by reference.

The locating module 108B is configured and operable as described above to provide an indication on the location of each section/portion of the substance in which fragments of the foreign element(s) were found. In an example, the locating module 108B indicates the location of sections/portions of the substance where the overall quantity of the foreign element(s) is higher than a preselected threshold. In a further example, the locating module 108B indicates the location of every section/portion of the substance in which one or more particular types of foreign elements (e.g. plastic products) are found in quantities higher than a preselected thresholds. Once located, those sections/portions which are heavily contaminated can be removed from the bulk for cleaning, separating the crop from plastic contaminants. In a different example, the inspection system 100A may be used for identifying the sources of the foreign elements, e.g. the sources of plastic contamination, and/or for assessing the quality of the substance (crop).

Figure 2C:
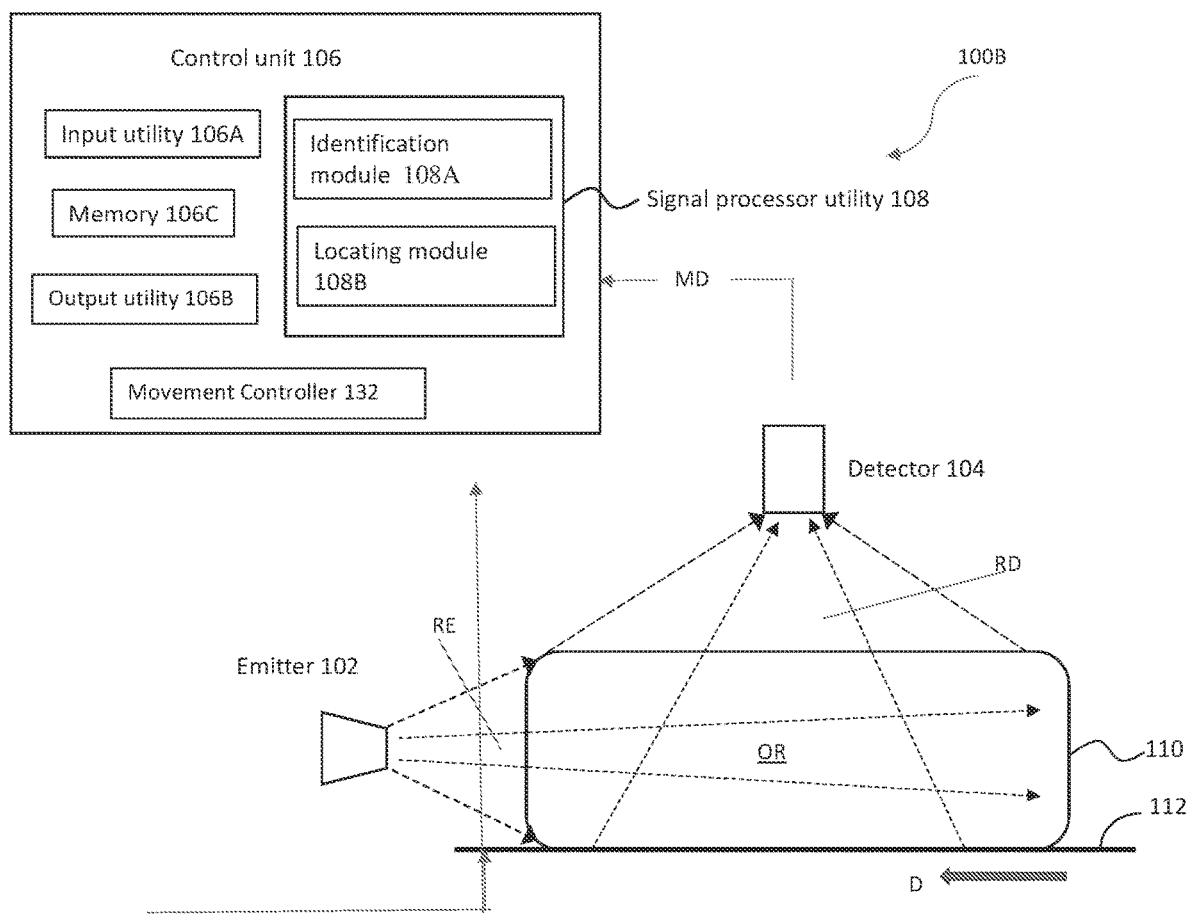
FIGS. 2C and 2D show two more examples of the configuration of FIG. 1.
Figure 2D:
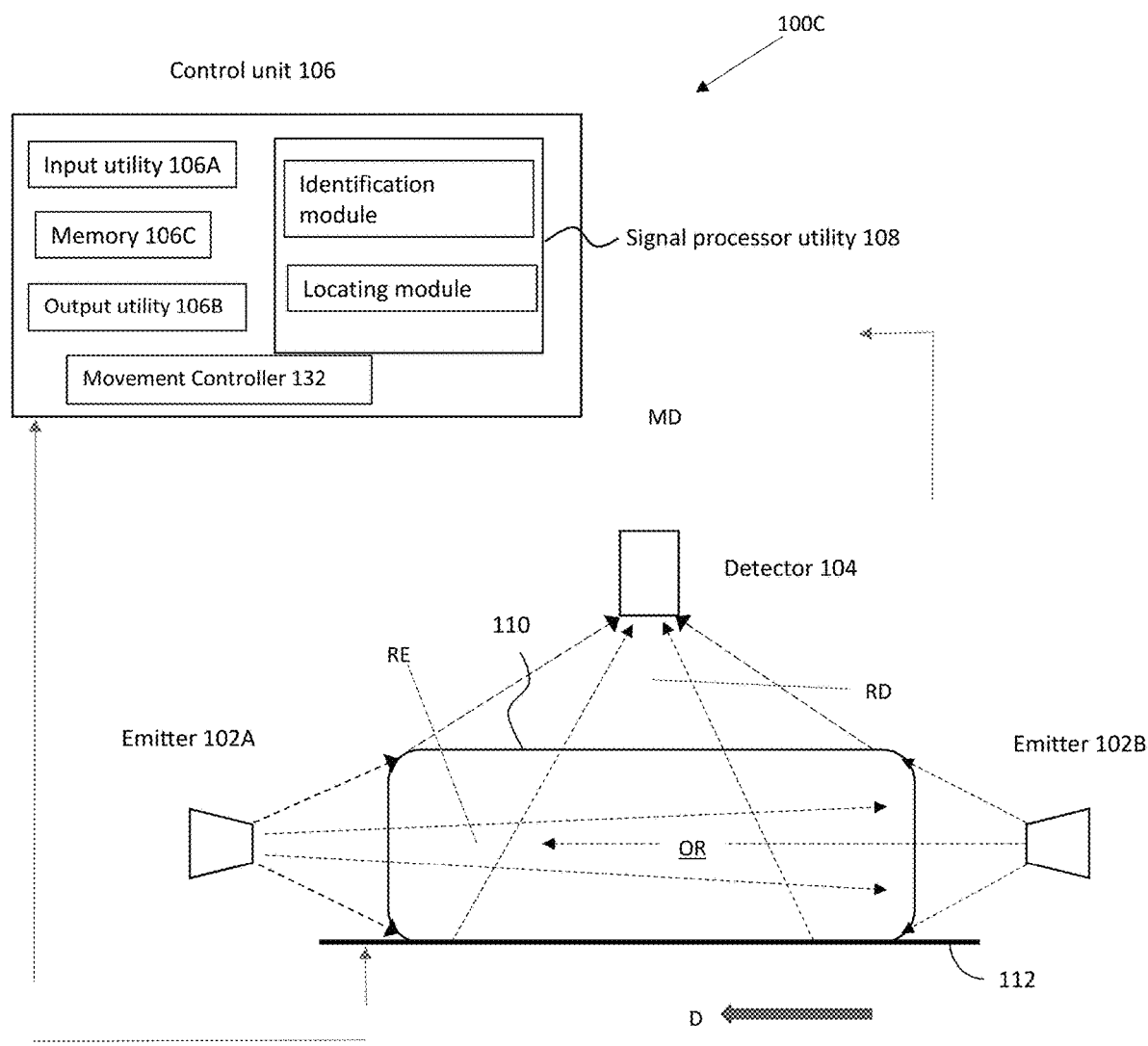

Reference is made to FIGS. 2C and 2D two more examples of the configuration and operation of the inspection system of the present invention. For simplicity, in these examples, the same reference numbers are used for identifying components which are common with the examples of FIGS. 2A and 2B.

In the example of FIG. 2C, an inspection system 100B is shown, which is configured generally similar to the above-described system 10, as well as the exemplary system 100A, namely the system 100B includes: a measurement device including a radiation source assembly (emitter) 102 and a detection assembly (detector) 104; and a control unit 106. The system 100B is used with a flow line arrangement, e.g. a continuous track 112 defining a movement path for the substance movement in a direction D towards the source and detector (towards and through the overlap region OR between the fields of view of the source and detector). The control unit 106 includes input and output utilities 106A and 106B, memory 106C, and signal processor 108, and a movement controller 132. The signal processor 108 includes an identification module 108A and a locating module 108B configured and operable as described above. The signal processor is configured as described above to process and analyze measured data MD provided by the detector, by utilizing reference data obtained from a database (e.g. in an external storage device), which is not specifically shown here. The system 100B is different from the previously described exemplary system 100A in that in the system 100B the configuration is such that the central axis of the solid angle of radiation detection RD is substantially perpendicular to a plane of the movement path, or in other words, the detector "looks" onto the top of surface of the substance, e.g. is positioned above the bulk of crop as it moves on a continuous track emitting radiation towards the top surface of the bulk of crop. As for the emitter assembly 102, the solid angle of radiation emission is directed towards one of the lateral sides of the movement path, to face one of the side surfaces of the substance (bulk).

In the example of FIG. 2D, an inspection system 100C is shown, which is different from the above described exemplary systems 100A and 100B in that the radiation source assembly 102 includes two emitter units associated with a single detector of the detection assembly 104. The emitter units 102A and 102B and oriented with respect to the movement path such that primary exciting radiation components of X-ray or Gamma-ray radiation emitted by the emitter units 102A and 102B are directed towards two opposite lateral sides of the movement path to irradiate two opposite surfaces of the substance (bulk of crop) being displaced along the movement path (on the continuous track) in a general movement direction D towards and through the overlap region OR between the fields of view of the sources and detector. Detector 104 is oriented with respect to the movement path similar to the above-described example of system 100B, i.e. the central axis of the solid angle of radiation detection RD is substantially perpendicular to a plane of the movement path, or in other words, the detector "looks" onto the top of surface of the substance, e.g. is positioned above the top surface of the bulk of crop. The radiation propagation channels for the primary radiation components emitted by the two emitters and for the X-ray response signals propagating to the detector overlap in the overlap region OR. The overall radiation emitted by the two emitter assemblies 102A and 102B may by of higher power (that is, emit more photons). Furthermore, as the two emitter assemblies 102A and 102B are located on opposite sides of the bulk, the radiation arriving at the bulk is more homogenous throughout the cross section of the bulk than in other configurations with single emitter assembly.

Figure 3:
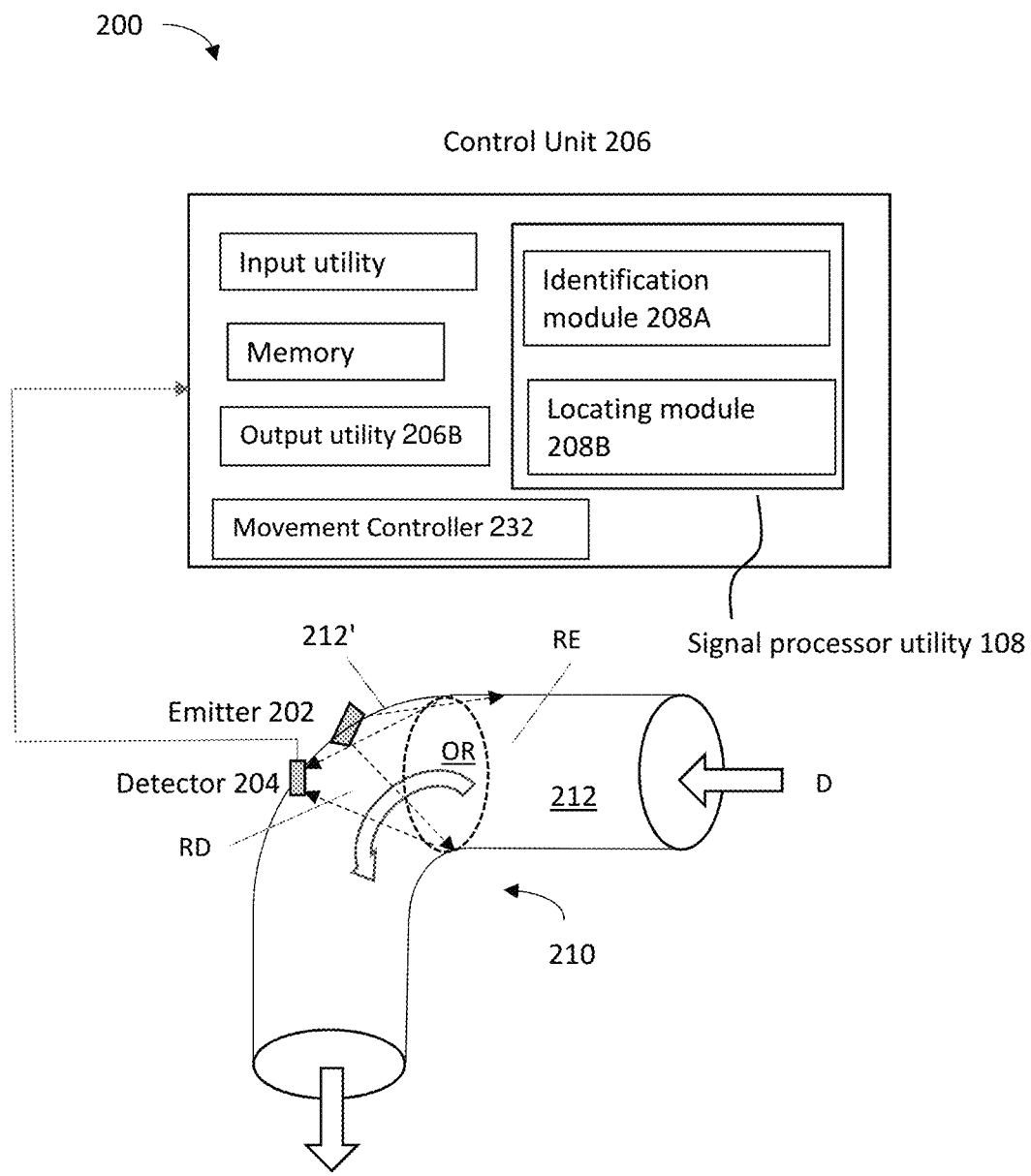
FIG. 3 is a schematic illustration of another example of the configuration of the system of FIG. 1, utilizing a curvilinear movement oath.

Reference is now made to FIG. 3 which is a schematic illustration of an exemplary inspection system 200 of the present invention, configured generally similar to the above described/exemplified systems, but in which the movement path 212 is a curvilinear path, namely has (at least) one curved portion 212' aligned with the boundary of the overlap region OR. Thus, the inspection system 200 includes: a measurement device including a radiation source assembly (emitter) 102 and a detection assembly (detector) 104; and a control unit 206. The measurement is configured for inspecting a substance during movement (flow) along the movement path in a general movement direction D towards and through the overlap region OR between the fields of view of the source and detector assemblies, where the overlap region is aligned with the curved region/portion. The control unit 206 includes input and output utilities 206A and 206B, memory 206C, and signal processor 208, and a movement controller 232. The signal processor 208 includes an identification module 208A and a locating module 208B configured and operable as described above. The signal processor is configured as described above to process and analyze measured data MD provided by the detector, by utilizing reference data obtained from a database (e.g. in an external storage device), which is not specifically shown here.

The system 200 may be used for identifying plastic contaminants within a load of crop as it moves inside the pipe towards, though and our of the overlap region OR. The emitter assembly 202 is configured for emitting X-ray or Gamma-ray radiation towards the substance (crop) moving inside the pipe 210. The substance may contain foreign element (plastic contaminants as fragments or shreds). The detector 204 detects X-ray response signals emitted from the markers in the foreign elements in response to excitation by said exciting radiation. The signal processor 206 is in communication with the detector 204 and is configured to detect and identify marked foreign elements in the successive portions of the substance moving through the pipe 210 (plastic contaminants within crop in the pipe). As described above, the signal processor 206 utilizes predetermined reference data in a database which may be stored in the memory 206C or external storage device, configured generally similar to that described above with reference to FIG. 1, where the reference data includes various marking signatures of marked foreign elements (plastic products) and the intensity of the response signal. The signal processor utility 208 may be configured and operable for identifying fragments of marked plastic products in the crop; and providing indication as to their position in the pipe. Data processing utility 208 may further include the identification module 208A adapted for analyzing data collected from the detector 204 and identifying XRF signatures of the various marked products found in the crop; and locating module 208B adapted for computing and providing indication on the location of plastic fragments in the crop.

In an embodiment of the present invention, the system 200 makes use of a pipe bend (curved region/portion) in order to improve the efficiency and accuracy of the measurements (detection and location) of marked foreign elements (plastic contaminants). The emitter assembly 202 and detector 204 are both positioned in the vicinity of the curved portion of the movement path (the pipe bend) with their apertures (solid angles of radiation emission and detection) facing the direction of substance movement along the movement path (facing the incoming crop), such that the emitter assembly 202 directs primary exciting X-ray or Gamma-ray radiation inside the pipe towards the substance (in a direction opposite to the movement direction of the substance), and the detector 204 detects the backscattered radiation (i.e. the X-ray response signal from the marked locations in the substance) propagating in the direction of the movement of the substance.

Such a system configuration exemplified in FIG. 3 (i.e. with the curvilinear movement path, formed by a relative displacement between the substance and the effective inspection zone defined by the overlap region) has a number of advantageous. As the substance (e.g. crop) flows towards the overlap region (towards the emitter 202 and the detector 204) measured data (counts of the detected X-ray response signals) is being generated during a time period from the point where the responsive foreign elements (markers) are close enough for the response signal to reach the detector 204 and up to the curved region of the movement path (pipe bend) where the detector 204 is positioned. Consequently, more data may be collected enhancing the accuracy of the measurement. Additionally, since the solid angles of the emission and detection of the emitter 202 and the detector 204, respectively, face (are directed towards) the cross section of the pipe and the crop load is advancing towards it, all the marked elements pass at the vicinity of the detector 204 (preventing a situation wherein foreign elements within the crop remain distant from the detector), reducing the probability of a marked element passing undetected. Furthermore, the intensity of the signal coming from the marked fragments increases as the fragments flow towards the detector 204 with a maximum at the point where the fragment is closest to the detector 204 at the point where the flow of the crop changes the flow direction. As shown in FIG. 3, the pipe bend may change the direction of the flow substantially perpendicularly, causing the crop and the marked fragments to exit the region/volume which is radiated by the emitter and/or the volume from which response signals may reach the detector. The intensity of the detectable response signal increases gradually as the marked fragment moves towards the detector 204 (depending on the velocity of flow of the crop) and drops much faster once the fragment reaches the closest point to the detector and then abruptly exits the volume irradiated by the emitter or the volume 'seen' by the detector. If the counts measured by the detector are collected in small enough time bins (e.g. fractions of a second), then the sudden decrease in the intensity of the response signal indicates with high accuracy the location of a section of the crop in the pipe where one or more marked fragments exist.

Placing the emitter assembly 202 and detector 204 within the pipe or attached to the pipe wall (such that radiation from the emitter assembly and response signals from the crop are emitted within the pipe) might be advantageous as this may require less shielding for blocking scattered radiation from reaching the vicinity of the system 200.

Figure 4:
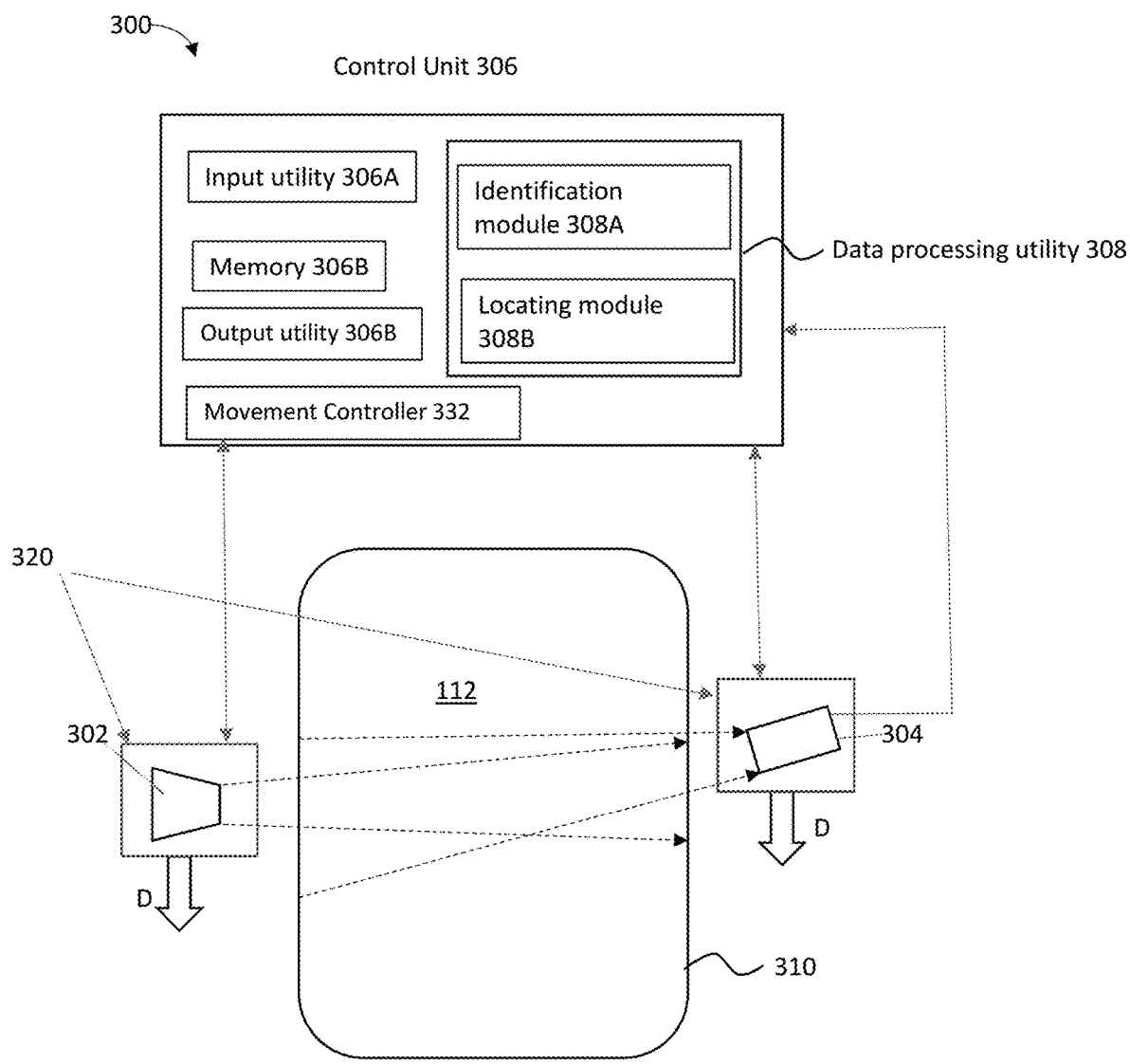
FIG. 4 is a schematic illustration of yet further example of the configuration of the system of the invention, in which radiation source and detection assemblies are translatable with respect to a movement path.

Reference is now made to FIG. 4 which is a schematic illustration of yet another embodiment of the invention. As inspection system 300 shown in the figure is generally similar to any of the above-described and exemplified system configurations, namely includes: a measurement device including a radiation source assembly (emitter) 302 and a detection assembly (detector) 304; and a control unit 306. The control unit 306 includes input and output utilities 306A and 306B, memory 306C, and signal processor 308, and a movement controller 332. The signal processor 308 includes an identification module 308A and a locating module 308B configured and operable as described above. The signal processor is configured as described above to process and analyze measured data provided by the detector, by utilizing reference data obtained from a database (e.g. in an external storage device), which is not specifically shown here. The system 300 may be used for identifying plastic contaminants within a bale of crop 310. The emitter assembly 302 is configured for emitting primary X-ray or Gamma-ray radiation towards a bale of crop 310; the bale of crop may contain plastic contaminants as fragments or shreds; and the detector 304 is configured for detecting X-ray response signals emitted from the plastic contaminants.

In this example, a flow line arrangement is provided including a translation assembly 320 comprising appropriate driver mechanism(s) (not shown here) operated by the movement controller 332 for controllably moving the emitter assembly 302 and/or the detector assembly 304, or preferably moving both of them, relative to the substance 310 (bale of crop). The source and/or detector is/are preferably moved in the direction D along an axis parallel to the movement path 112, thus scanning the substance.

The bale of crop 310 may be a bale of harvested crop before processing (for example a bale of cotton before it is processed in a cotton gin) or a bale of crop after processing, for example a bale of compressed cotton after processing in the gin). The bale 310 may be commonly stationary, while the emitter assembly 302 together with the detector assembly 304 move relative to the bale of crop 310 scanning the bale. The emitter assembly 302 may move along one or more axes parallel to at least one lateral side of the movement path, i.e. to at least one surface of the bale, while emitting the primary X-ray or Gamma-ray radiation towards the bale 310, and the detector 304 may move along the parallel axis (on the opposite side of the movement path) along one or more surfaces of the bale 310 simultaneously with the emitter assembly' movement, thus detecting the response signals emitted from the marked plastic fragments within the bale 310. In order to minimize the amount of (primary) radiation arriving directly from the emitter assembly 302 to the detector 304, the detector 304 is not positioned exactly opposite the emitter assembly 302 (on the axis defined by the direction of the beam of radiation emitted by the emitter assembly 302), but is slightly spaced from the axis and its aperture is directed to a slightly different axis.

In some embodiments, the emitter assembly 302 and the detector 304 are configured to continuously emit and detect radiation, respectively, while scanning the bale. Data collected by the detector 304 is stored in memory 308B and processed by the signal processor 306. The signal processor utility 308 operates to identify in the measured data the X-ray response signals corresponding to XRF signatures of one or more marked plastic products indicating the presence and possibly the source of plastic contamination within the bale 310. The measured data collected by the detection assembly 304 may be collected for the duration of a preselected time period or a sequence of time periods (time bins) corresponding to successively scanned sections of the bale or alternatively for the entire duration of the scanning of the bale (corresponding to the bale). Therefore, in an example the system 300 may be configured to provide indication on the quantity of marked plastic contaminants in each section of bales. In a different example, the system 300 is configured to provide indication on the quantity of marked plastic contaminants in the entire bale. In an aspect of the system 300 may provide indication as to types of plastic fragments and their possible sources (that is the plastic product from which they originate) in the bale or possibly in each section of the bale.

Thus, the present invention provides a novel approach for inspecting a substance to detect and identify (and preferably also locate) foreign element(s) in the substance during a relative displacement between the substance and one or more elements of the inspection system. The principles of the invention are not limited to any specific type of substance, as well as not limited to any specific foreign element, provided the foreign element is of the type carrying an X-ray responding material(s).

The invention claimed is:

1. A system for detecting and identifying at least one predetermined foreign element in a substance, the system comprising:

a measurement device comprising: a radiation source assembly comprising at least one source of X-ray radiation or Gamma-ray radiation, each source of the at least one source being configured to generate X-ray radiation or Gamma-ray radiation having predetermined properties and a predetermined solid angle of radiation emission to excite a portion of the substance located in a region within the predetermined solid angle of radiation emission to cause an X-ray response of the portion of the substance; a radiation detection assembly comprising at least one detector having a solid angle of radiation detection overlapping with the predetermined solid angle of radiation emission, each detector of the at least one detector being configured and operable to detect an X-ray radiation propagating within a solid angle of radiation detection and generate measured data indicative of the X-ray response of the portion of the substance, including a relative displacement between the substance and at least one of the radiation source assembly and the radiation detection assembly along a movement path; the measurement device being configured and operable such that the measured data is indicative of a time variation of the X-ray response of the portion of the substance;

a flow line arrangement comprising a translation assembly configured and operable for translating at least one of the radiation source assembly and the radiation detection assembly with respect to the movement path; and a control unit configured and operable for a data communication with the radiation detection assembly to receive and analyze the measured data, the control unit comprising a signal processor configured and operable to identify in the measured data a pattern of a signal variation over time indicative of a location of at least one foreign element carrying an X-ray responsive marker in the substance.

2. The system according to claim 1, wherein the movement path passes through a vicinity of an overlap region between the solid angle of radiation detection and the predetermined solid angle of radiation emission.

3. The system according to claim 1, wherein the flow line arrangement further comprises a support platform for supporting the substance and moving the substance with respect to the at least one of the radiation source assembly and the radiation detection assembly.

4. The system according to claim 1, wherein the translation assembly is configured and operable for translating both the radiation source assembly and the radiation detection assembly with respect to the movement path.

5. The system according to claim 4, wherein the translation assembly is configured and operable for simultaneously translating the radiation source assembly and the radiation detection assembly such that the predetermined solid angle of radiation emission and the solid angle of radiation detection are oriented towards two opposite lateral sides of the movement path.

6. The system according to claim 1, wherein the radiation source assembly and the radiation detection assembly are oriented with respect to the movement path such that the predetermined solid angle of radiation emission and the solid angle of radiation detection oppose a direction of a movement of the substance along the movement path, such that when the substance moves through an overlap region a distance between the substance and each of the radiation source assembly and the radiation detection assembly is being reduced.

7. The system according to claim 6, wherein the pattern of the signal variation over time indicative of the location of the at least one foreign element carrying the X-ray responsive marker in the substance is characterized by a non-symmetric characteristic signal peak indicative of the location of the at least one foreign element carrying the X-ray responsive marker in the substance, the non-symmetric characteristic signal peak having a moderate signal intensity rise when the distance between the substance and each of the radiation source assembly and the radiation detection assembly is being reduced, and a sharp signal intensity fall when the location of the at least one foreign element carrying the X-ray responsive marker in the substance exits the overlap region, thereby enabling to accurately identify the location of the at least one foreign element carrying the X-ray responsive marker in the substance along at least one dimension.

8. The system according to claim 7, wherein the signal processor is configured and operable to integrate the measured data indicative of the X-ray response of the portion of the substance being detected over time, while the at least one foreign element is being moved through the overlap region, thereby emphasizing the non-symmetric characteristic signal peak.

9. The system according to claim 1, wherein the movement path is a substantially linear path.

10. The system according to claim 1, wherein the movement path has a curvilinear path having at least one curved portion aligned with a boundary of an overlap region.

11. The system according to claim 1, wherein the radiation source assembly and the radiation detection assembly are accommodated at opposite lateral sides of the movement path, thereby yielding a reduced variation in a detected signal intensity of the X-ray response of the portion of the substance, irrespective of a lateral location of the at least one foreign element carrying the X-ray responsive marker in the substance while in an overlap region.

12. The system according to claim 11, wherein the radiation source assembly and the radiation detection assembly are accommodated at opposite lateral sides of the movement path such that the X-ray radiation or Gamma-ray radiation and the X-ray response of the portion of the substance being detected vary with a distance from the radiation source assembly and the radiation detection assembly.

13. The system according to claim 1, wherein the signal processor is configured and operable to identify the at least one foreign element carrying the X-ray responsive marker in the substance by analyzing the X-ray response of the portion of the substance over a database storing X-ray signatures corresponding to multiple known X-ray responsive markers.

14. The system according to claim 1, wherein the at least one foreign element carrying the X-ray responsive marker in the substance to be identified comprises one or more plastic elements carrying one or more X-ray responsive markers.

15. The system according to claim 14, wherein the signal processor is configured and operable to process the measured data and generate data indicative of a quantity of the one or more plastic elements within at least a portion of the substance.

16. The system according to claim 1, wherein the at least one source of X-ray radiation or Gamma-ray radiation comprises at least two sources of X-ray radiation or Gamma-ray radiation, each of the at least two sources having the predetermined solid angle of radiation emission oriented with respect to the movement path to irradiate a different side surface of the substance, and the solid angle of radiation detection of the at least one detector oriented to detect the X-ray radiation propagating from a top surface of the substance.

17. The system according to claim 1, wherein the at least one detector comprises at least two detectors having solid angles of radiation detection are oriented with respect to the movement path to detect the X-ray radiation propagating from two opposite side surfaces of the substance, and the predetermined solid angle of radiation emission of the at least one source of X-ray radiation or Gamma-ray radiation is oriented to irradiate a top surface of the substance.

18. The system according to claim 1, wherein the radiation source assembly and the radiation detection assembly are accommodated with respect to the movement path such that the predetermined solid angle of radiation emission and the solid angle of radiation detection are oriented towards two different surfaces of the substance.

\* \* \* \* \*